(12) United States Patent
Kojima

(10) Patent No.: US 10,321,814 B2
(45) Date of Patent: Jun. 18, 2019

(54) IMAGE PICKUP APPARATUS AND ENDOSCOPE

(71) Applicant: OLYMPUS CORPORATION, Tokyo (JP)

(72) Inventor: Kazuaki Kojima, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 90 days.

(21) Appl. No.: 15/706,681

(22) Filed: Sep. 16, 2017

(65) Prior Publication Data

US 2018/0000327 A1   Jan. 4, 2018

Related U.S. Application Data

(63) Continuation of application No. PCT/JP2015/059961, filed on Mar. 30, 2015.

(51) Int. Cl.
| | |
|---|---|
| *A61B 1/04* | (2006.01) |
| *A61B 1/05* | (2006.01) |
| *H04N 7/18* | (2006.01) |
| *H01L 27/14* | (2006.01) |
| *H04N 5/225* | (2006.01) |

(52) U.S. Cl.
CPC .............. *A61B 1/04* (2013.01); *A61B 1/051* (2013.01); *H01L 27/14* (2013.01); *H04N 5/225* (2013.01); *H04N 5/2253* (2013.01); *H04N 7/18* (2013.01); *H04N 2005/2255* (2013.01)

(58) Field of Classification Search
None
See application file for complete search history.

(56) References Cited

U.S. PATENT DOCUMENTS 5,130,804 A * 7/1992 Tamura ............... G11B 17/032
348/231.7
2010/0321565 A1   12/2010 Motohara et al.
(Continued)

FOREIGN PATENT DOCUMENTS

| JP | 2004-62048 A | 2/2004 |
| JP | 2008-118568 A | 5/2008 |

(Continued)

OTHER PUBLICATIONS

International Search Report dated Jun. 23, 2015 in PCT/JP2015/059961.

*Primary Examiner* — Fernando Alcon
(74) *Attorney, Agent, or Firm* — Scully, Scott, Murphy & Presser, P.C.

(57) ABSTRACT

An image pickup apparatus includes: an image pickup device that includes a light receiving surface, an opposite surface, a light receiving portion, and external electrodes connected to the light receiving portion; and a wiring board that includes a first main surface, a second man surface, and a wiring portion provided with first bonding electrodes bonded to the external electrodes, wherein the first main surface of the wiring portion is arranged at a first angle θ1 equal to or smaller than 90 degrees relative to the opposite surface, the wiring board includes a reinforced portion and a folded portion bent at the first angle θ1 between the reinforced portion and the wiring portion, and the second main surface of the reinforced portion is fixed to the opposite surface of the image pickup device.

10 Claims, 7 Drawing Sheets

(56) References Cited

U.S. PATENT DOCUMENTS

| | | | |
|---|---|---|---|
| 2011/0211053 A1* | 9/2011 | Nakayama | A61B 1/051 348/76 |
| 2011/0249106 A1* | 10/2011 | Makino | H04N 5/2254 348/76 |
| 2015/0228678 A1* | 8/2015 | Yoshida | A61B 1/00071 600/110 |
| 2018/0040652 A1* | 2/2018 | Maeda | H01L 27/14618 |
| 2018/0041666 A1* | 2/2018 | Nakayama | H01L 27/14 |
| 2018/0368661 A1* | 12/2018 | Suyama | A61B 1/04 |
| 2019/0000307 A1* | 1/2019 | Kawahara | A61B 1/04 |

FOREIGN PATENT DOCUMENTS

| | | |
|---|---|---|
| JP | 2009-188802 A | 8/2009 |
| JP | 2009-295825 A | 12/2009 |
| JP | 2010-258582 A | 11/2010 |
| JP | 2014-75764 A | 4/2014 |
| WO | 2009/098937 A1 | 8/2009 |
| WO | 2014/054419 A1 | 4/2014 |

* cited by examiner

IMAGE PICKUP APPARATUS AND ENDOSCOPE

CROSS REFERENCE TO RELATED APPLICATION

This application is a continuation application of PCT/JP2015/059961 filed on Mar. 30, 2015, the entire contents of which are incorporated herein by this reference.

BACKGROUND OF THE INVENTION

1. Field of the Invention

The present invention relates to an image pickup apparatus and an endoscope including the image pickup apparatus, the image pickup apparatus including: an image pickup device in which a plurality of electrodes electrically connected to a light receiving portion are lined up; and a wiring board in which a plurality of first bonding electrodes respectively bonded to the plurality of electrodes of the image pickup device are lined up on an end portion.

2. Description of the Related Art

An image pickup apparatus created by wafer level CSP technology is small, and this significantly contributes to a reduction in the diameter of an endoscope.

In a manufacturing method of an image pickup apparatus of a wafer level CSP type, a plurality of light receiving portions and a plurality of external electrodes electrically connected to the respective light receiving portions are first formed on a light receiving surface of a semiconductor wafer. The light receiving portions are pixel areas formed by CMOS (complementary metal oxide semiconductor) image sensors, CCDs (charge coupled devices), or the like. A glass wafer is adhered to the light receiving surface of the semiconductor wafer to create a bonding wafer. A plurality of through-wires are formed from a light receiving surface of the bonding wafer to an opposing opposite surface.

A light receiving surface of an image pickup device obtained by cutting the bonding wafer is covered by a cover glass. However, the light receiving portions are connected to electrodes on the opposite surface through the through-wires, and electrical signals can be transmitted and received.

An image pickup apparatus 101 shown in FIG. 1 is disclosed in Japanese Patent Application Laid-Open Publication No. 2014-75764. In the image pickup apparatus 101, a plurality of wires are arranged on one through-trench 110T, in place of the plurality of through-wires.

The image pickup apparatus 101 includes: an image pickup device 110 to which a cover glass 130 is adhered through an adhesive layer 120; a wiring board 140; and signal cables 150. A plurality of electrode pads 113 (bumps 114) respectively connected to external electrodes 112 of a light receiving surface 110SA are lined up on an inclined wall surface (inclined surface) 110SS of the through-trench 110T of the image pickup device 110. Note that the inclined surface 110SS is inclined at a first inclination angle θ1 that is an acute angle, relative to the light receiving surface 110SA of the image pickup device 110.

The plurality of electrode pads 113 are respectively bonded to a plurality of bonding electrodes 141 lined up on an end portion of a main surface 140SA of the wiring board 140 through the bumps 114. That is, the main surface 140SA of the wiring board 140 is inclined at the first inclination angle θ1 relative to an opposite surface 110SB of the image pickup device 110. The signal cables 150 are bonded to bonding electrodes (not shown) on the other end portion of the wiring board 140.

In the image pickup apparatus 101, the image pickup device 110 and the wiring board 140 are fixed only through bonding portions of the electrode pads 113 and the bonding electrodes 141.

SUMMARY OF THE INVENTION

An embodiment of the present invention provides an image pickup apparatus including: an image pickup device including: a light receiving surface; an opposite surface opposing the light receiving surface; a light receiving portion configured to receive light entering from the light receiving surface; and a plurality of external electrodes electrically connected to the light receiving portion; and a wiring board including a first main surface, a second main surface opposing the first main surface, and a wiring portion arranged on a side of the opposite surface of the image pickup device, the wiring portion being provided with a plurality of bonding electrodes respectively bonded to each of the plurality of external electrodes, wherein the first main surface of the wiring portion is arranged at a first angle equal to or smaller than 90 degrees relative to the opposite surface of the image pickup device, the wiring board includes: a reinforced portion; and a folded portion bent at the first angle between the reinforced portion and the wiring portion, and the second main surface of the reinforced portion of the wiring portion is fixed to the opposite surface.

Another embodiment of the present invention provides an endoscope including an image pickup apparatus on a distal end portion of an insertion portion, the image pickup apparatus including: an image pickup device including: a light receiving surface; an opposite surface opposing the light receiving surface; a light receiving portion configured to receive light entering from the light receiving surface; and a plurality of external electrodes electrically connected to the light receiving portion; and a wiring board including a first main surface, a second main surface opposing the first main surface, and a wiring portion arranged on a side of the opposite surface of the image pickup device, the wiring portion being provided with a plurality of bonding electrodes respectively bonded to each of the plurality of external electrodes, wherein the first main surface of the wiring portion is arranged at a first angle equal to or smaller than 90 degrees relative to the opposite surface of the image pickup device, the wiring board includes a reinforced portion, and a folded portion bent at the first angle between the reinforced portion and the wiring portion, and the second main surface of the reinforced portion of the wiring portion is fixed to the opposite surface.

DETAILED DESCRIPTION OF THE PREFERRED EMBODIMENT(S)

First Embodiment

Hereinafter, an image pickup apparatus 1 according to a first embodiment of the present invention will be described with reference to the drawings. Note that the drawings are schematic drawings, and a relationship between a thickness and a width of each member, a ratio of the thickness of respective members, the number of electrode pads, arrangement pits, and the like are different from the reality. The relationship and the ratio of respective dimensions between the drawings are different in some parts of the drawings. Furthermore, part of the configuration, such as a silicon oxide layer and wires on a surface of a silicon substrate, is not illustrated.

Figure 1:
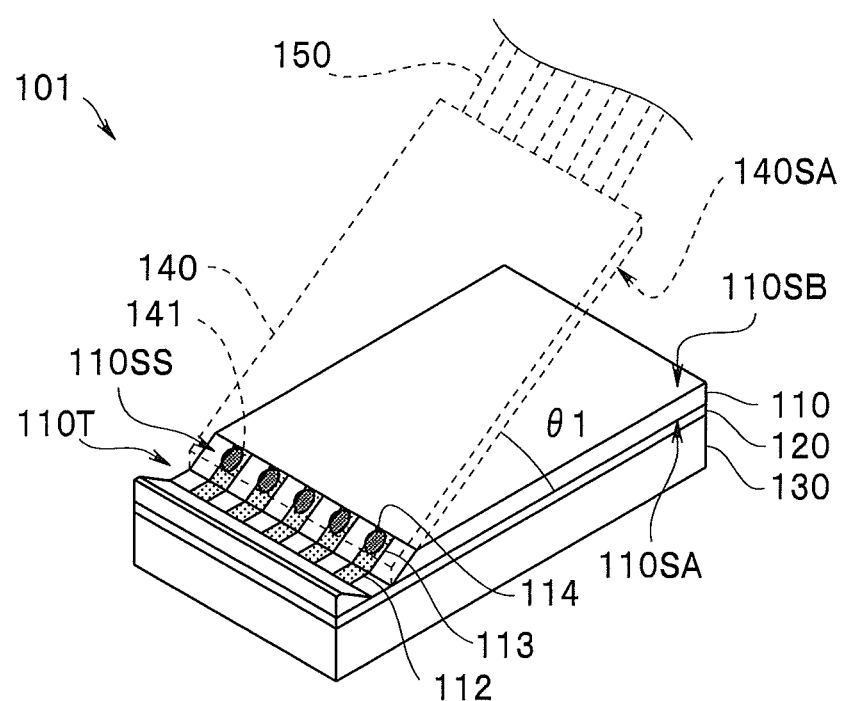
FIG. 1 is a perspective view of a conventional image pickup apparatus.
Figure 2:
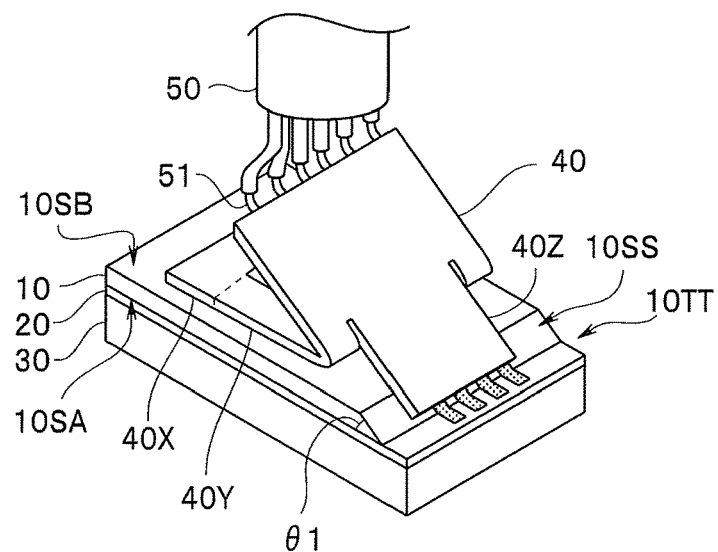
FIG. 2 is a perspective view of an image pickup apparatus of a first embodiment.
Figure 3:
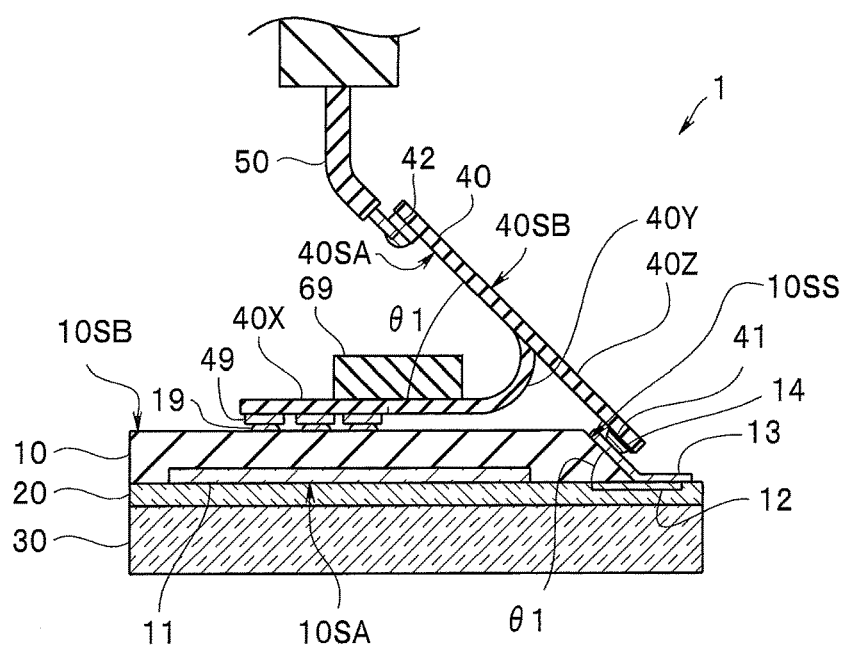
FIG. 3 is a cross-sectional view of the image pickup apparatus of the first embodiment.

As shown in FIGS. 2 and 3, the image pickup apparatus 1 includes: an image pickup device 10 formed by a silicon substrate; a cover glass 30 that is a transparent member; a wiring board 40; and a signal cable 50. The image pickup apparatus 1 is covered by the cover glass 30 through an adhesive layer 20, which is made of a transparent material, of a light receiving surface 10SA of the image pickup device 10.

The image pickup device 10 has substantially the same configuration as the configuration of the image pickup device 110 of the conventional image pickup apparatus 101 already described. However, in the image pickup device 10, a notch 10TT, not a through trench (10T), forms a wall surface of an inclined surface MSS inclined at the first angle θ1 relative to the light receiving surface 10SA. That is, when a cut line for cutting the bonding wafer is on a bottom surface of the through-trench, the through-trench becomes the notch 10TT after the cut.

On a bottom surface of the notch 10TT of the image pickup device 10, back surfaces of external electrodes 12 electrically connected to a light receiving portion 11 are exposed. A plurality of electrode patterns 13 (solder bumps 14) respectively and electrically connected to the external electrodes 12 are lined up on the inclined surface 10SS. The electrode patterns 13 are electrically connected to the light receiving portion 11 through the external electrodes 12. Note that a plurality of first conductor patterns 19 each including a solder bump are arranged in a matrix on an opposite surface 10SB of the image pickup device 10, in the same way as a plurality of second conductor patterns 49 (see FIG. 4) of the wiring board 40.

Figure 4:
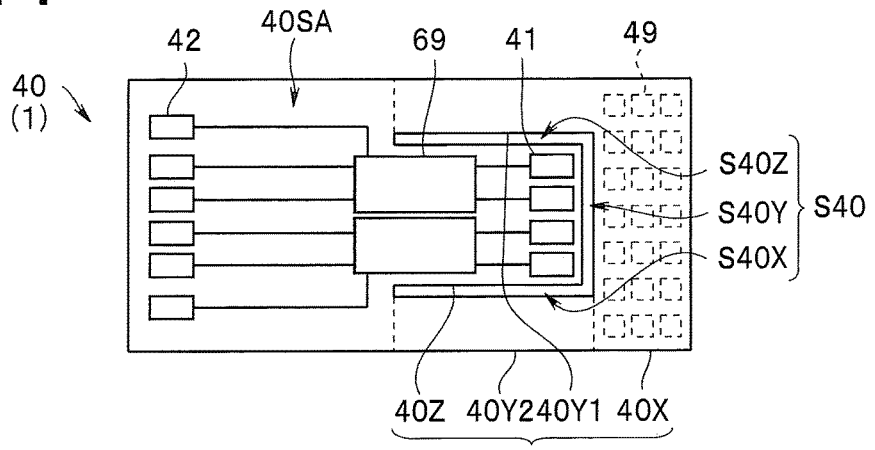
FIG. 4 is a top view of a wiring board of the image pickup apparatus of the first embodiment.

On the other hand, as shown in FIG. 4, the wiring board 40 with flexibility is partitioned by slits S40 into a wiring portion 40Z, a reinforced portion 40X, and folded portions 40Y (40Y1, 40Y2). The slits S40 are square-U-shaped and include: a first slit S40X and a third slit S40Z parallel to a long axis direction of the wiring board 40; and a second slit S40Y formed in a short axis direction and connecting a distal end of the first slit S40X and a distal end of the third slit S40Z.

A back side of the second slit S40Y is the wiring portion 40Z, lateral sides of the first slit S40X and the third slit S40Z are the folded portions 40Y1 and 40Y2, and a front side of the second slit S40Y is the reinforced portion 40X. Note that boundaries between the wiring portion 40Z, the folded portions 40Y1 and 40Y2, and the reinforced portion 40X are illustrated by broken lines for the description in FIG. 4 and the like, but the boundaries are not strictly defined.

A plurality of first bonding electrodes 41 are lined up on a front end portion of a first main surface 40SA of the wiring portion 40Z. In other words, a direction of the arrangement of the first bonding electrodes 41 is a forward direction of the wiring board 40. Second bonding electrodes 42 are lined up on a back end portion.

Note that electronic components 69 are mounted on the first main surface 40SA. Note that the electronic components 69 may also be mounted on a second main surface 40SB.

The plurality of second conductor patterns 49 are arranged in a matrix on the second main surface 40SB of the reinforced portion 40X. As already described, the arrangement of the plurality of second conductor patterns 49 corresponds to the arrangement of the plurality of first conductor patterns 19 of the image pickup device 10.

The wiring board 40 is, for example, a flexible wiring board including polyimide as a base. Although the wiring board 40 may be a non-flexible substrate made of a glass epoxy resin or the like, at least the folded portions 40Y need to be flexible. Note that as described later, it is preferable that the wiring board 40 be a flexible substrate in order to house the wiring board 40 in a projection surface of the image pickup device 10.

Figure 5:
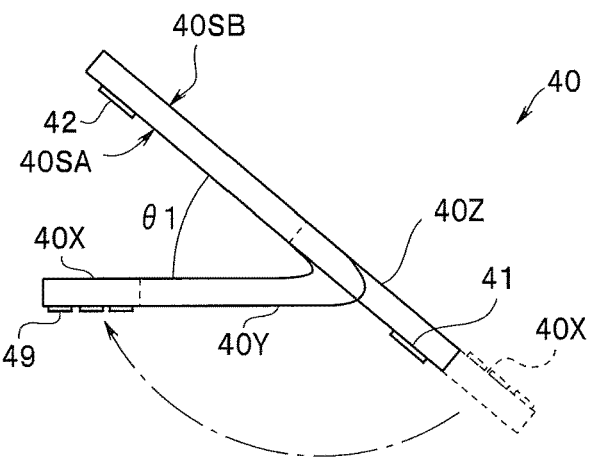
FIG. 5 is a cross-sectional view for describing a manufacturing method of the wiring board of the image pickup apparatus of the first embodiment.

As shown in FIG. 5, the reinforced portion 40X of the wiring board 40 is folded in a direction of the first main surface 40SA through the folded portions 40Y. The folding angle is the first angle θ1 that is the same as the inclination angle of the inclined surface 10SS of the image pickup device 10.

The first bonding electrodes 41 of the wiring board 40 are bonded to the electrode patterns 13 of the inclined surface 10SS of the image pickup device 10 through the solder bumps 14. Therefore, the main surface of the wiring portion 40Z of the wiring board 40 is inclined at the first angle θ1 relative to the opposite surface 10SB of the image pickup device 10.

On the other hand, the second bonding electrodes 42 on the back end portion of the wiring board 40 are bonded to conducting wires 51 of the signal cable 50. Note that the first bonding electrodes 41 and the second bonding electrodes 42 are electrically connected through the electronic components 69 mounted on the main surface 40SA or wires (not shown).

Note that bonding sections of the first bonding electrodes 41 and the electrode patterns 13 may be sealed by a sealing resin to increase the reliability of bonding. However, it may not be easy to sufficiently secure the mechanical strength just by the sealing resin that fixes only the bonding sections.

However, in the image pickup apparatus 1, the second conductor patterns 49 of the reinforced portion 40X of the wiring board 40 are soldered and bonded to the first conductor patterns 19 on the opposite surface 10SB of the image pickup device 10. That is, solder bumps or the like are provided on the first conductor patterns 19 or the second conductor patterns 49 although not shown.

In the image pickup apparatus 1, the wiring board 40 is partitioned by the slits into the wiring portion 40Z, the reinforced portion 40X fixed to the opposite surface 10SB of the image pickup device 10, and the folded portions 40Y1 and 40Y2 folded at the first angle θ1. The wiring board 40 in a planar state forms a three-dimensional shape when the folded portions 40Y1 and 40Y2 are folded, and the angle formed by the main surface of the reinforced portion 40X and the main surface of the wiring portion 40Z is the first angle θ1.

In the image pickup apparatus 1, the image pickup device 10 and the wiring board 40 are fixed not only at the bonding sections of the first bonding electrodes 41 and the electrode patterns 13, but the opposite surface 10SB and the reinforced portion 40X arranged in parallel are also fixed. Therefore, the image pickup apparatus 1 is unlikely to be damaged when the apparatus is handled. The image pickup apparatus 1 is inexpensive because manufacturing is easy, and the yield is high.

Note that an adhesive may be used to fix the reinforced portion 40X of the wiring board 40 and the opposite surface 10SB of the image pickup device 10. A resin may also be filled between the wiring board 40 and the image pickup device 10 to further increase the mechanical strength between the wiring board 40 and the image pickup device 10.

In the image pickup apparatus 1, the entirety of the wiring board 40 and the signal cables 50 positioned on a back side of the image pickup device 10 (opposite side of the cover glass 30) is arranged in a region inside of the image pickup device 10, that is, in the projection surface of the image pickup device 10, in plan view of the image pickup device 10 in a thickness direction. Particularly, when the wiring board 40 is flexible, the wiring board 40 can be bent and deformed to arrange the entire wiring board 40 in the projection surface of the image pickup device 10 even if the length of the wiring board 40 is long. The diameter of the image pickup apparatus 1 is small because the wiring board 40 and the signal cable 50 do not protrude outside of the external form of the image pickup device 10.

<Modifications>

Next, image pickup apparatuses 1A to 1C according to modifications of the first embodiment will be described. Note that the image pickup apparatuses 1A to 1C are similar to the image pickup apparatus 1. Therefore, the same reference signs are provided to the components with the same functions, and the description will be omitted.

<Modification 1>

Figure 6:
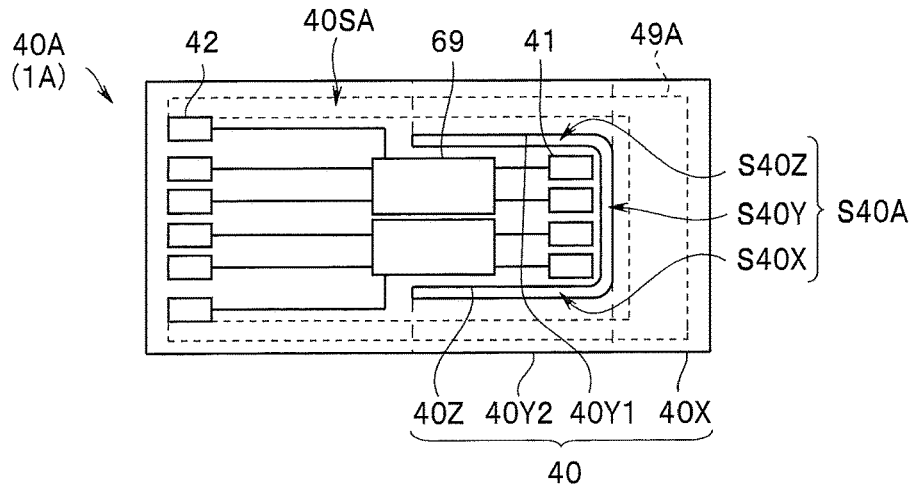
FIG. 6 is a top view of a wiring board of an image pickup apparatus according to modification 1 of the first embodiment.

As shown in FIG. 6, the slit S40X of a wiring board 40A of the image pickup apparatus 1A of modification 1 is U-shaped. That is, a connection portion of the first slit S40X and the second slit S40Y and a connection portion of the third slit S40Z and the second slit S40Y are curved. Furthermore, second conductor patterns 49A with large areas are provided on the second main surface 40SB of the reinforced portion 40X. Although not shown, a plurality of solder bumps are arranged in a matrix on the second conductor patterns 49A.

The second conductor patterns 49A are bonded to the opposite surface of the image pickup device and the first conductor patterns, and the image pickup device and the wiring board 40A are fixed.

Note that in the image pickup apparatus 1A, the second conductor patterns 49A are extended to the back end portion of the wiring board 40 through the folded portions 40Y (40Y1, 40Y2). The signal cable 50 is bonded to the back end portion of the second conductor patterns 49A.

In the image pickup apparatus 1A, heat generated by the image pickup device 10 is transferred from the opposite surface 10SB through the solder and the second conductor patterns 49A with high thermal conductivity. The temperature of the image pickup device is unlikely to become high, and the image pickup apparatus 1A is unlikely to be adversely affected by the heat compared to the image pickup apparatus 1. Therefore, the stability of the image pickup apparatus 1A is excellent.

<Modification 2>

Figure 7:
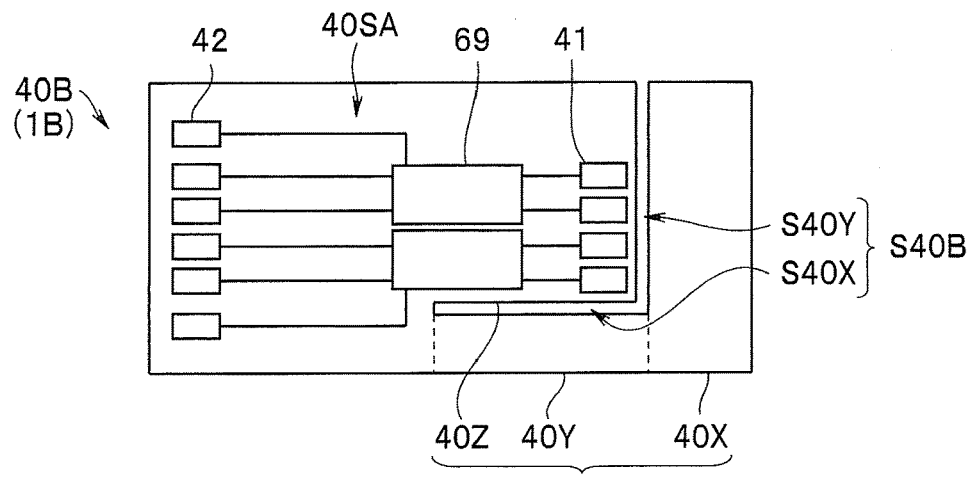
FIG. 7 is a top view of a wiring board of an image pickup apparatus according to modification 2 of the first embodiment.

As shown in FIG. 7, slits S40B of a wiring board 40B of the image pickup apparatus 1B according to modification 2 are L-shaped. That is, the slits S40B include the first slit S40X parallel to the long axis direction and the second slit S40Y extended in the short axis direction from the distal end of the first slit S40X. The back side of the second slit S40Y is the wiring portion 40Z, the lateral side is the folded portion 40Y, and the front side is the reinforced portion 40X.

<Modification 3>

Figure 8:
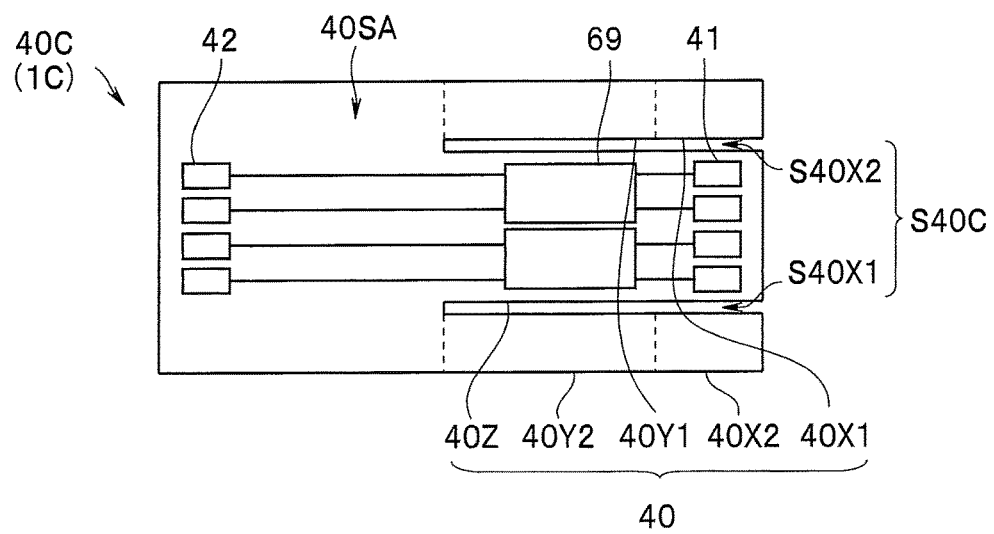
FIG. 8 is a top view of a wiring board of an image pickup apparatus according to modification 3 of the first embodiment.

As shown in FIG. 8, slits S40X1 and S40X2 parallel to the long axis direction are formed on a wiring board 40C of the image pickup apparatus 1C according to modification 3. Front portions of the slits S40X1 and S40X2 are reinforced portions 40X1 and 40X2, back portions are the folded portions 40Y1 and 40Y2, and inside of the two slits S40X1 and S40X2 is the wiring portion 40Z.

The reinforced portions 40X1 and 40X2 are fixed to the opposite surface of the image pickup device.

In the image pickup apparatuses 1A to 1C of modifications 1 to 3, the wiring board is partitioned by the slits into the wiring portion, the reinforced portion, and the folded portion as in the image pickup apparatus 1, and the folded portion is folded to form a three-dimensional shape.

That is, although not shown, the main surface of the wiring portion 40Z of all of the image pickup apparatuses 1A to 1C of modifications 1 to 3 is arranged at the first angle θ1 equal to or smaller than 90 degrees relative to the opposite surface 10SB of the image pickup device 10. The second conductor patterns 49A of the wiring portion 40Z are bonded to the first conductor patterns on the opposite surface of the image pickup device, and the image pickup device and the wiring board 40A are fixed.

Therefore, the image pickup apparatuses 1A to 1C are inexpensive because manufacturing is easy, and the yield is high, as in the image pickup apparatus 1.

Second Embodiment

Next, an image pickup apparatus 1D of a second embodiment will be described. Note that the image pickup apparatus 1D is similar to the image pickup apparatus 1. Therefore, the same reference signs are provided to the components with the same functions, and the description will be omitted.

Figure 9:
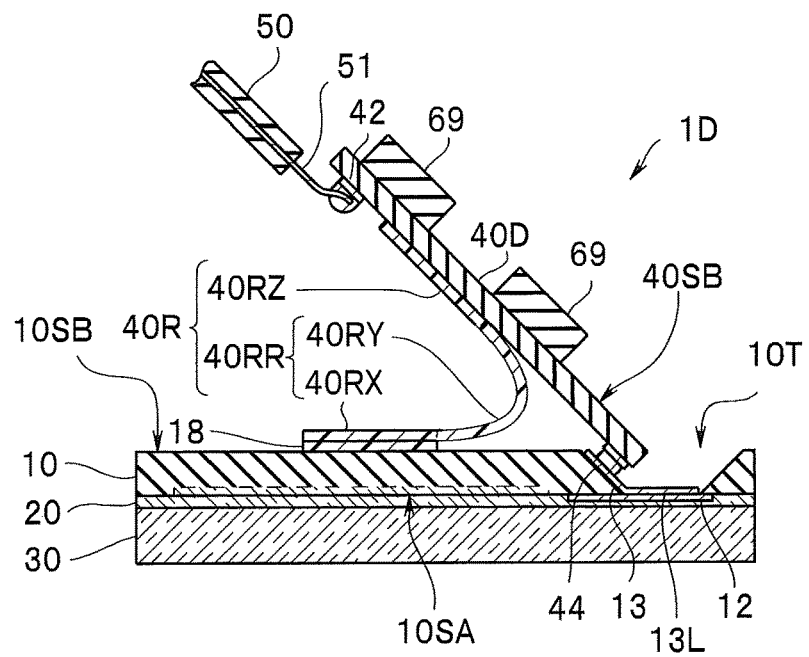
FIG. 9 is a cross-sectional view of an image pickup apparatus of a second embodiment.
Figure 10:
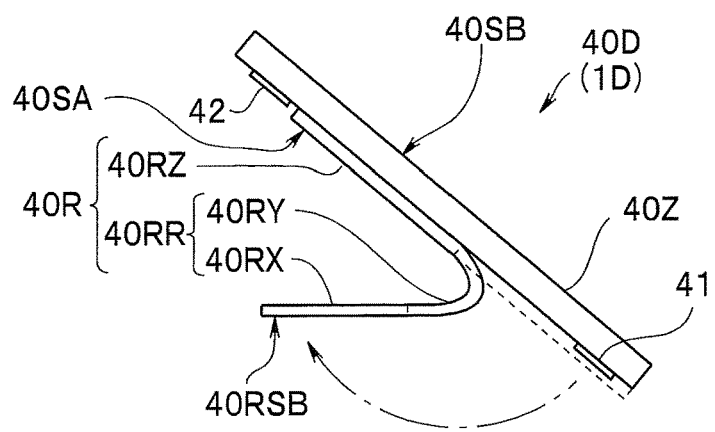
FIG. 10 is a cross-sectional view for describing a manufacturing method of a wiring board of the image pickup apparatus of the second embodiment.

As shown in FIGS. 9 and 10, a wiring board 40D of the image pickup apparatus 1D includes a separation layer 40R at a top layer of the first main surface 40SA, the separation layer 40R partially separated from a layer directly under. In the separation layer 40R, a separated separation portion 40RR is a reinforced portion 40RX and a folded portion 40RY, and a part not separated is a fixed portion 40RZ. A second main surface 40RSB of the reinforced portion 40RX is adhered to the opposite surface 10SB of the image pickup device 10 through an adhesive layer 18.

The separation layer 40R is made of, for example, a resin film laminated by a thermo-compression bonding method at the top layer of the wiring board 40D. The separation portion 40RR is a part not bonded by thermo-compression in the lamination.

The image pickup apparatus 1D has advantageous effects of the image pickup apparatus 1, and furthermore, more first bonding electrodes 41 can be lined up in a width direction of the wiring board 40D compared to the image pickup apparatus 1. In addition, the width of the wiring board can be easily reduced to equal to or smaller than the width of an image pickup device even in the image pickup device with a narrow width.

Note that the separation layer 40R is not limited to the laminated film, and the separation layer 40R may be a metal layer at the top layer of the wiring board or may be a resin layer provided with the metal layer. The top layer of the wiring board detached from the layer directly under serves as the separation layer 40R. An image pickup apparatus in which the separation layer 40R including a metal layer with high thermal conductivity is fixed to the image pickup device 10 through soldering can efficiently transfer the heat generated by the image pickup device 10.

Third Embodiment

Next, an image pickup apparatus 1E of a third embodiment will be described. Note that the image pickup apparatus 1E is similar to the image pickup apparatus 1. Therefore, the same reference signs are provided to the components with the same functions, and the description will be omitted.

Figure 11:
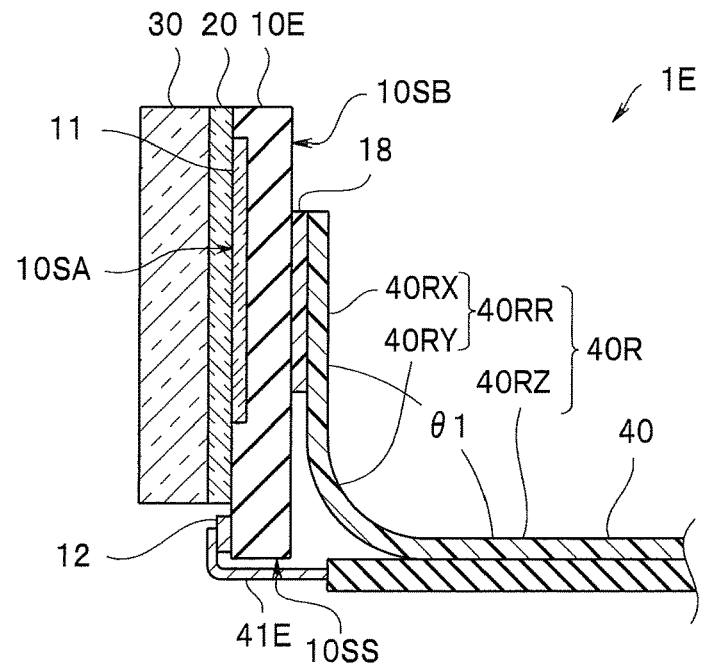
FIG. 11 is a cross-sectional view of an image pickup apparatus of a third embodiment.

As shown in FIG. 11, the region provided with the external electrodes 12 on the light receiving surface 10SA is not covered by the cover glass 30 in an image pickup device 10E of the image pickup apparatus 1E. The entire side surface of the image pickup device 10E is orthogonal to the light receiving surface 10SA. In other words, the first angle $\theta 1$ that is the inclination angle of the inclined surface 10SS is 90 degrees.

Figure 12:
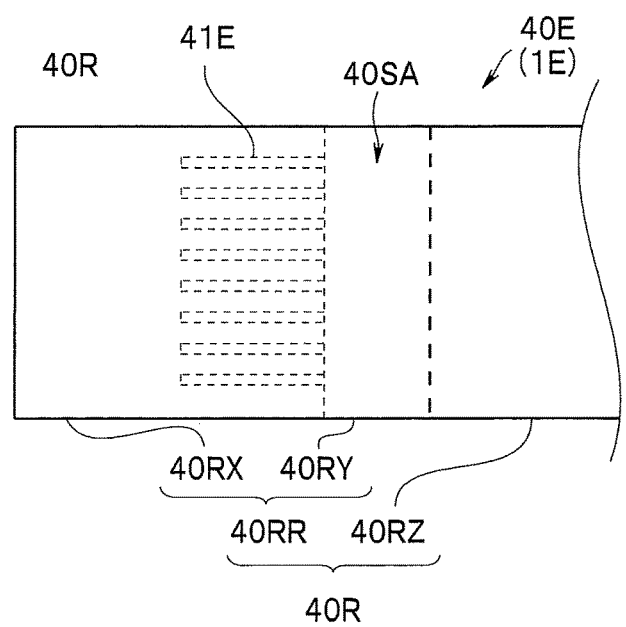
FIG. 12 is a top view of a wiring board of the image pickup apparatus of the third embodiment.

On the other hand, as shown in FIGS. 11 and 12, bonding electrodes lined up on an end surface of a wiring board 40E are flying leads 41E folded substantially at a right angle. The flying leads 41E are called outer leads in a lead frame and are formed by conductor wires in which an insulation base of the wiring board 40E is selectively removed. The separation layer 40R formed by a resin film is laminated at the top layer of the wiring board 40E.

The flying leads 41E can be easily folded substantially at a right angle. Therefore, the flying leads 41E bonded to the external electrodes 12 on the light receiving surface 10SA of the image pickup device 10E are folded substantially at 90 degrees and arranged in a parallel direction of the side surface 10SS.

The part 40RR of the separation layer 40R separated from the layer directly under in the wiring board 40E is the folded portion 40RY and the reinforced portion 40RX. The part not separated is the fixed portion 40RZ. In the image pickup apparatus 1E, the folded portion 40RY is folded at the first angle $\theta 1$, that is, 90 degrees, which is the inclination angle of the inclined surface 10SS. The reinforced portion 40RX is arranged parallel to the opposite surface 10SB of the image pickup device 10E and fixed through the adhesive layer 18.

The image pickup apparatus 1E has the same advantageous effects as the advantageous effects of the image pickup apparatus 1 and the like. That is, when the first main surface 40SA provided with the wires of the wiring board 40E as a wiring portion is arranged at the first angle $\theta 1$ equal to or smaller than 90 degrees relative to the opposite surface 10SB of the image pickup device 10E, the folded portion 40RY can be folded at the first angle $\theta 1$ to bond the reinforced portion 40RX to the opposite surface 10SB.

Note that it is obvious that distal end portions of the wires can also be the flying leads 41E in the image pickup apparatuses 1 and 1A to 1D. The image pickup device 10E and the wiring board 40E may be fixed through soldering in the image pickup apparatus 1E.

Fourth Embodiment

Lastly, an endoscope 2 of a fourth embodiment will be described. The endoscope 2 includes one of the already described image pickup apparatuses 1 and 1A to 1E. Therefore, the same reference signs are provided to the same components, and the description will be omitted.

Figure 13:
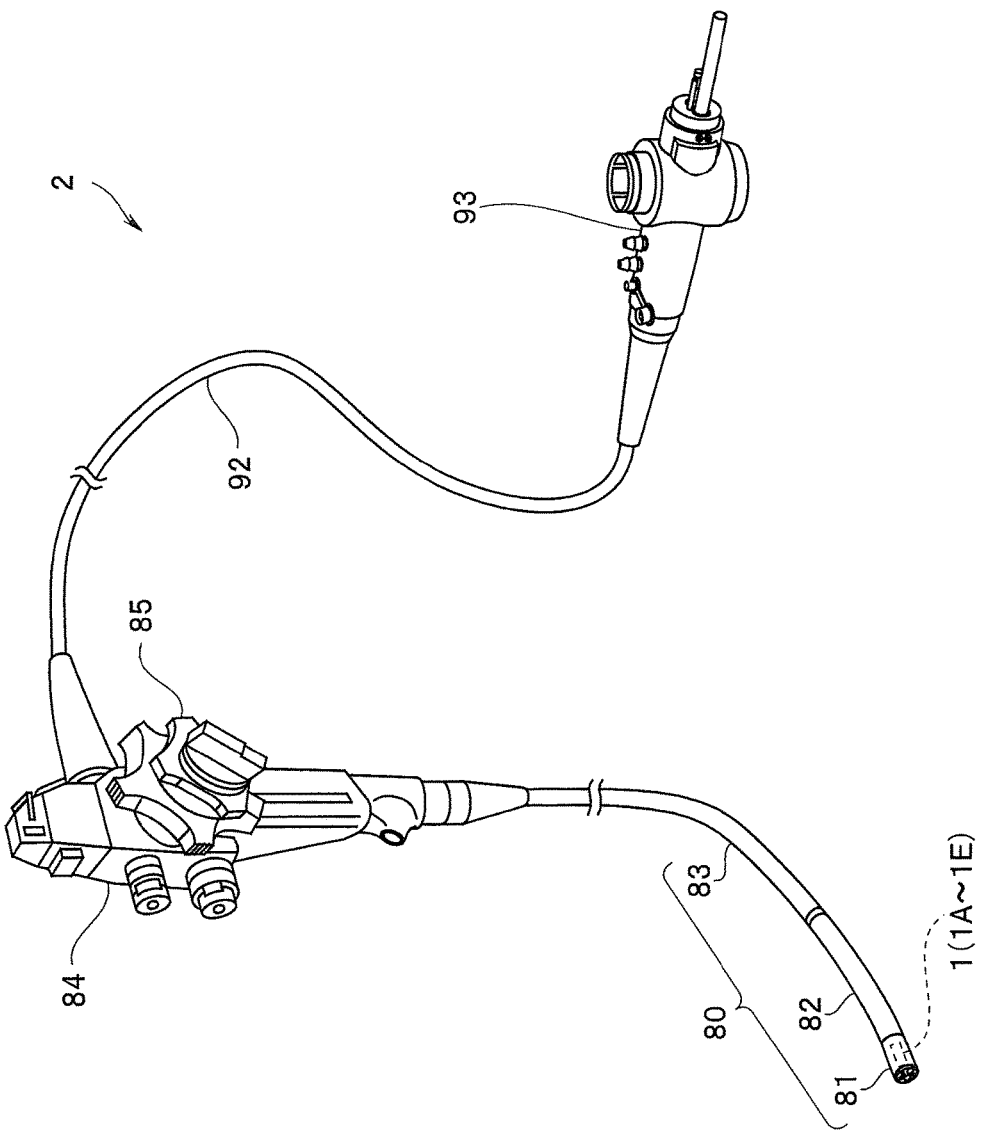
FIG. 13 is a perspective view of an endoscope of a fourth embodiment.

As shown in FIG. 13, the endoscope 2 of the present embodiment is an electronic endoscope including: an insertion portion 80; an operation portion 84 provided on a proximal end portion side of the insertion portion 80; a universal cord 92 extended from the operation portion 84; and a connector 93 provided on a proximal end portion side of the universal cord 92. In the insertion portion 80, a rigid distal end portion 81, a bending portion 82 for changing a direction of the rigid distal end portion 81, and a long and narrow flexible portion 83 with flexibility are sequentially and continuously connected.

The rigid distal end portion 81 is provided with the image pickup apparatus 1 (1A to 1E). When the image pickup apparatus 1 (1A to 1E) is provided in a narrow space of the rigid distal end portion 81, unexpected stress may be applied. However, the image pickup apparatus 1 (1A to 1E) is unlikely to be damaged when the apparatus is handled. Note that after the arrangement on the rigid distal end portion 81, the image pickup apparatus 1 (1A to 1E) is fixed and sealed in the rigid distal end portion 81 by a sealing resin. Therefore, no problem arises in the bonding strength between the image pickup device 10 and the wiring board 40 during the use of the endoscope 2.

The endoscope including the image pickup apparatus 1 (1A to 1E) with a high yield that can be easily manufactured can be easily manufactured, and the yield is high.

The present invention is not limited to the above-described embodiments, the modifications, and the like, and various changes, alterations, combinations, and the like can be made without departing from the scope of the present invention.

What is claimed is:

1. An image pickup apparatus comprising:
   an image pickup device comprising: a light receiving surface; an opposite surface opposing the light receiving surface; a light receiving portion being configured to receive light entering from the light receiving surface; and a plurality of external electrodes electrically connected to the light receiving portion; and
   a wiring board comprising a first main surface, a second main surface, and a wiring portion arranged on a side of the opposite surface of the image pickup device, the wiring portion being provided with a plurality of bonding electrodes respectively bonded to each of the plurality of external electrodes, wherein the first main surface of the wiring portion is arranged at a first angle equal to or smaller than 90 degrees relative to the opposite surface of the image pickup device, the wiring board comprises: a reinforced portion; and a folded portion bent at the first angle between the reinforced portion and the wiring portion, and the second main surface of the reinforced portion of the wiring portion is fixed to the opposite surface.

2. The image pickup apparatus according to claim 1, wherein the wiring portion, the reinforced portion, and the folded portion are partitioned by slits formed on the wiring board.

3. The image pickup apparatus according to claim 2, wherein the slits comprising a first slit parallel to a long axis direction and a second slit extended in a short axis direction from a distal end of the first slit are formed on the wiring board, a back side of the second slit is the wiring portion, a lateral side of the slits is the folded portion, and a front side of the slits is the reinforced portion.

4. The image pickup apparatus according to claim 3, wherein the slits have a U shape or a square-U shape, and comprise a third slit parallel to the first slit, wherein a distal end of the third slit is connected to another distal end of the second slit.

5. The image pickup apparatus according to claim 1, wherein the image pickup device includes a first conductor pattern on the opposite surface, the wiring board includes a second conductor pattern on the second main surface, and the second conductor pattern of the reinforced portion is soldered and bonded to the first conductor pattern.

6. The image pickup apparatus according to claim 5, wherein the second conductor pattern is extended to a back part of the wiring portion through the folded portion.

7. The image pickup apparatus according to claim 1, wherein the wiring board comprises a separation layer at a top layer of the first main surface, the separation layer being partially separated from a layer directly under, and the reinforced portion and the folded portion are formed by a separation portion of the separation layer.

8. The image pickup apparatus according to claim 1, wherein the plurality of external electrodes are provided on a side surface of the image pickup device, the side surface being inclined at the first angle that is an acute angle, relative to the light receiving surface.

9. The image pickup apparatus according to claim 1, wherein the plurality of external electrodes are provided on the light receiving surface of the image pickup device, and the plurality of bonding electrodes are flying leads bonded to the plurality of external electrodes.

10. An endoscope comprising the image pickup apparatus according to claim 1 on a distal end portion of an insertion portion.

* * * * *